United States Patent [19]

Nagji et al.

[11] Patent Number: 4,734,199
[45] Date of Patent: Mar. 29, 1988

[54] LIQUID PHASE ADSORPTION PROCESS

[75] Inventors: Moez M. Nagji, Yonkers; Olaf Nifontoff, Stony Point, both of N.Y.

[73] Assignee: Union Carbide Corporation, Danbury, Conn.

[21] Appl. No.: 932,370

[22] Filed: Nov. 19, 1986

[51] Int. Cl.⁴ ............................................. B01D 15/00
[52] U.S. Cl. .................................. 210/674; 210/677; 210/690; 585/824
[58] Field of Search .................. 208/310 R, 310 Z; 210/670, 674, 677, 690; 585/822–824

[56] References Cited

U.S. PATENT DOCUMENTS 2,985,589 5/1961 Broughton et al. ............ 208/310 R
3,489,808 1/1970 Eberly ............................ 585/824

Primary Examiner—Ivars Cintins
Attorney, Agent, or Firm—Richard G. Miller

[57] ABSTRACT

An improved liquid phase adsorption process is provided using a fixed bed system wherein the conventional post-regeneration bed-filling step and the post-adsorption bed-draining step are replaced by a displacement step. The bed volume of regeneration medium in a first bed of the system undergoing the final stage of regeneration cool-down is passed directly into a second bed of the system in the final stage of the adsorption step whereby the bed volume of void-space feedstock in said second bed is removed therefrom by displacement, thus effectively accomplishing in a single operation the filling step in the first bed and the draining step in the second bed.

8 Claims, 2 Drawing Figures

LIQUID PHASE ADSORPTION PROCESS

BACKGROUND OF THE INVENTION

1. Field of the Invention

The present invention relates in general to adsorption separation processes, and more particularly to adsorption separation processes carried out in a fixed bed adsorption system comprising at least two beds wherein the fluid employed to cool an adsorption bed after regeneration is different from the fluid feedstock being treated and wherein the end of the cooling step the regenerated bed is filled with cooling fluid and another of the beds is filled with feedstock, said feedstock and cooling fluid being both in the liquid phase. In such processes, the drain and fill steps, conventionally carried out as discrete operations, are combined and integrated as a single displacement step.

2. DESCRIPTION OF THE PRIOR ART

As practiced in accordance with the prior art, an overall process cycle carried out in the liquid phase and using fixed adsorbent beds of particulate adsorbent could comprise as many as six distinct steps, namely:

(a) adsorption of one or more components from a feedstock mixture:

(b) draining the bed of unprocessed feedstock;

(c) regeneration of the bed using a heated purge fluid;

(d) cooling down the newly regenerated bed in preparation for a new adsorption step by passage into the bed of a cooling medium:

(e) draining the cooling medium from the cooled bed; and (f) filling the void space of the cooled bed with fresh feedstock.

These steps are more fully characterized below:

Adsorption Step (a): During this step the liquid phase feedstock containing the impurities to be removed is passed through a vessel containing a suitable particulate adsorbent such as a zeolitic molecular scene. As the feed passes through the adsorbent bed the impurities (sorbates) are selectively held up by the adsorbent. The feed, now containing significantly less impurity, leaves the adsorption vessel as product. The adsorption step is continued for a fixed time interval or until the impurity levels in the product exceed specifications. At this time the feed is directed to another adsorption vessel of the system, this vessel having been previously regenerated.

Feedstock Drain Step (b): During this drain step, the feedstock remaining in the void space of the vessel at the end of the adsorption step (a) is drained by gravity or pumped out and recycled to feed. If the vessel is drained slowly then the time required for draining will constitute a significant portion of the overall cycle time. If the vessel is drained quickly then the additional flow rate due to material combining with the feed must be considered when sizing the sorbent requirement. In either case, the elimination of the drain step would be of considerable advantage in a liquid phase sorption system.

Regeneration Heat Step (c): After draining step (b), a heated regeneration medium is passed through the adsorbent bed. As the adsorbent is heated it releases the previously sorbed sorbate. The sorbate passes into the regeneration heating medium and is carried out of the system by the latter. The heating step is continued until the bulk of the impurities have been carried out of the adsorption vessel. Regeneration heating is usually carried out with a regenerating medium differing from both product and feedstock.

Regeneration-Cool Step (d): During this step a cooling medium is passed through the hot adsorption vessel to carry out the sensible heat remaining in the adsorption vessel at the end of the regeneration heat step. The cooling is continued until the bulk of sensible heat is carried out of the sorption vessel. In many instances cooling is carried out with a medium other than the feedstock. It is customary to drain this medium before proceeding to the fill step. This adds another step to the overall process cycle.

Cooling Medium Drain Step (e) the step in which the cooling medium remaining in the adsorbent bed void space at the end of Regeneration Cool Step (d) is removed from the bed either by gravity flow or by pumping.

Void Space Filling Step (f): During the fill step, either product or feedstock is used to fill the void spaces in the adsorption vessel before returning the vessel back into service. This is necessary since failure to do so will result in two phase flow and vapor lock. In large volume sorption vessels the time required for filling the vessel can be substantial especially since often the rate at which feed or product is available is often limited.

Upon completion of the fill step the sorption vessel is ready to be put back into the sorption step.

From the preceding description it is apparent that the sorption step must be of long enough duration so that the other sorption vessel(s) can be drained, heated, cooled, and filled before being placed back into service. For such systems sorption processes can become prohibitively expensive and are not competitive with other available separation processes because large sorbent inventories must be used.

SUMMARY OF THE INVENTION

The present invention resides in an improved cyclic adsorption process which comprises the steps of (a) providing an adsorption system comprising at least a first and a second fixed adsorbent bed containing adsorbent particles:

(b) passing as a feedstock into the first of said adsorbent beds a mixture of at least two molecular species in the liquid phase of which at least one is selectively adsorbed by the adsorbent particles, and recovering from the bed a product having a lower concentration of the adsorbed species than the feedstock:

(c) terminating the passage of feedstock into said first adsorbent bed at a time when the adsorbent therein retains sufficient capacity to adsorb the desired amount of the molecular species from the feedstock remaining within the said first adsorbent bed, and directing the flow of the said feedstock in the liquid phase into the second of said fixed adsorbent beds, said second bed at the beginning of passage of feedstock thereinto containing in the void space a liquid purge medium different from the feedstock in step (b), and preferably being at substantially the same temperature as said first bed at the beginning of step (c) therein;

(d) recovering said liquid purge medium from the void space of said second bed by displacement as a result of the passage of feedstock thereinto and passing said displaced liquid purge medium directly and preferably in the same direction or flow as in step (b) to the said first bed as said first bed exists at the beginning of step (c) above, whereby the feedstock in the void space of said first bed is purged therefrom and (e) continuing the flow of feedstock into said second bed as in the same manner as in (b) and recovering a product of essentially the same composition as is recovered in step (b).

DETAILED DESCRIPTION OF THE INVENTION

The process of the present invention is carried out in the liquid phase and using a cooling fluid which is different from the feedstock being treated. In those circumstances in which the cooling medium is the same as the feedstock being treated, there is no need either to drain the cooled adsorption bed of feedstock or to drain the bed of such feedstock before commencing the next adsorption phase of the process. While the purified product resulting from treating the feedstock is different from the feedstock and accordingly can suitably be employed in the practice of this invention, the greatest advantages are derived from the process when the cooling medium is neither the feedstock being treated or the purified product.

The feedstocks suitably treated by the present process are not a narrowly critical factor, it being the principal properties of such feedstocks that are normally in the liquid phase under the pressure conditions which can reasonably be imposed on the adsorption system. Also the feedstocks must contain a constituent, preferably a minor constituent, which is selectively adsorbed by the sorbent employed. Such feedstocks include mixtures of hydrocarbons where the sorptive selectivity is based on molecular size, degree of unsaturation or degree of volatility. The selectively adsorbed impurity can be a non hydrocarbon such as water, alcohols, sulfides, nitrogen containing compounds and organometallics. It has been found that the process is highly beneficial in the removal of methanol from the raffinate of a distillation column used to recover product methyl tert. butyl ether formed in the reaction between methanol and isobutylene. The illustration of the invention below is concerned with such a process.

The particulate adsorbent involved is also not a critical feature. Any of the commonly used solid adsorbents such as activated alumina, silica gel, or zeolitic molecular sieves can be employed.

The temperature and pressure conditions to be utilized are in the main dependent upon the feedstocks being treated and the adsorbent employed. In general the temperature at which the adsorption purification step is carried out is, when possible, at ambient or room temperature since lower temperatures favor adsorption but higher or lower temperatures can be used. Pressure conditions are chosen to maintain the feedstocks and purge and cooling streams in the liquid phase and to move the fluids through the system at the desired rates. The degree to which the regeneration purge streams are elevated in temperature is also largely dependent upon the particular adsorbate being removed from the sorbent and also the particular sorbent employed. The selection of all of these operating parameters is well within the routine skill of those familiar with the adsorption purification art.

Figure 1:
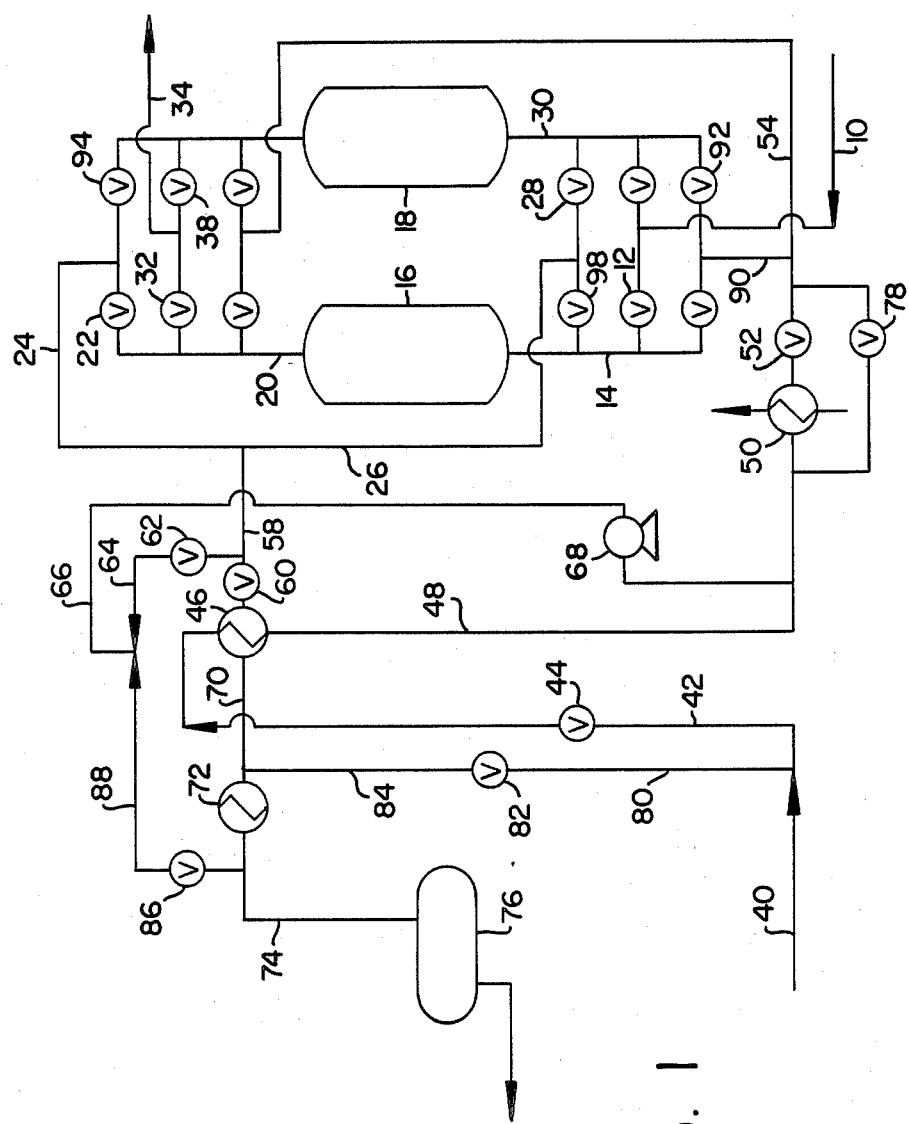
FIG. 1 of the drawings is a schematic flow diagram of an adsorption system suitable for the practice of the present invention, comprising two adsorbent beds coupled with appropriate conduits and valves.

The invention is illustrated by the following process description made with reference to the flow diagram of FIG. 1 of the drawings: The feedstock being treated in this illustrative process is the overhead effluent from the distillation tower in an overall process for preparing methyl tert.-butyl ether (MTBE). This overhead effluent is obtained by the catalyzed reaction of isobutylene with a stoichiometric excess of methanol in the liquid phase at a temperature of about 65° C. to about 90° C. The isobutylene reactant is introduced into the reactor as a mixture with other $C_4$ hydrocarbons including butene-1, cis and trans butene-, butadiene, isobutane and n-butane. The isobutylene constitutes about 10 mol % of the $C_4$ hydrocarbon mixture, and is the only $C_4$ species which reacts with the methanol under the present conditions. The molar ratio of methanol to isobutylene is from about 2:1 to 10:1. The effluent from the reactor comprises product MTBE, unreacted methanol, unreacted $C_4$'s and small to trace amounts of dimethylether and other reaction by products. This effluent is passed to a distillation unit wherein the MTBE product is recovered from the bottom. The overhead effluent from the distillation tower comprises from about 0.5 to 4.0 volume percent unreacted methanol, unreacted $C_4$ hydrocarbons, 200 to 400 ppm (v.) dimethylether and other volatile products, and is hereinafter referred to as the feedstock. In the operation of this illustrative process the overall cycle requires 160 minutes, i.e., that is the time interval required from the beginning of an adsorption-purification step in one of the adsorption beds until the beginning of the next adsorption-separation step in the same bed. With respect to the drawing, feedstock enters the system through line 10 in the liquid phase at a temperature of about 50° C. and under a pressure of about 150 psia. The feedstock passes through valve 12 and line 14 to adsorbent bed 16 containing zeolitic molecular sieve adsorbent having capacity to adsorb methanol. A preferred adsorbent for this purpose is the commercial zeolite widely known as zeolite X. It has been surprisingly found that silica gel exhibits exceptional performance as an adsorbent in the liquid phase processes of this invention and, accordingly, is also a preferred adsorbent. The temperature within adsorption bed 16 is at an initial temperature of about 50° C. Immediately prior to introduction of the feedstock into bed 16, the bed contains one bed volume of the liquid regeneration cool-down medium as a result of the immediately prior regeneration of bed 16. This regeneration cool-down medium is a portion of the same $C_4$ hydrocarbon mixture which is, along with methanol, fed to the upstream MTBE reactor. The bed regeneration procedure is described hereinafter with respect to adsorbent bed 18. The flow of feedstock into bed 16 continues for a total period of 80 minutes, during which time methanol is adsorbed selectively and retained in the bed. For the first thirty minutes of that period, the effluent from bed 16 is principally the regeneration cool down medium which filled the bed immediately prior to the beginning of the feedstock flow thereinto. Over this thirty-minute period, the regeneration medium effluent passes through line 20, valve 22, lines 24 and 26, valve 28 and line 30 into the bottom of bed 18. Thereafter for the remaining fifty minutes of the aforesaid eighty minute flow period of feedstock into bed 16, the effluent through line 20 is $C_4$ hydrocarbon product essentially free of methanol, and is passed through valve 32 and line 34 either out of the system for further treatment such as dimethylether removal.

At the beginning of the passage of the feedstock into bed 16, bed 18 has completed the adsorption-purification step except that there remains in the bed void space about one bed volume of feedstock. Flow of feedstock into bed 18 has been terminated at the point where the adsorbent therein retains sufficient capacity to adsorb the amount of methanol present in the void space feedstock. In conventional practice this bed volume of feedstock would be drained from the bed using a discrete draining step, and thereafter the bed regeneration would begin. In the present process, however, the drain step is avoided by using the bed volume of void space regeneration cool down medium which is the effluent from bed 16 at this time to force the bed volume of feedstock in bed 18 upward over the unspent adsorbent therein and out of bed 18 as product effluent free of methanol. Such product stream of $C_4$ hydrocarbons is passed from bed 18 through line 36, valve 38 and line 34. This displacement stage requires thirty minutes, and thereafter for the next fifty minutes, bed 18 is regenerated countercurrently by the passage of a heated liquid stream of $C_4$ hydrocarbon, which as noted hereinabove, is a portion of the same $C_4$ hydrocarbon stream fed to the MTBE reactor along with methanol. This reqeneration medium enters the system of the drawing at line 40, and passes through line 42, valve 44, heat exchanger 46, wherein its temperature is raised somewhat by cross exchange with hot regeneration medium returning from bed 18, thence through line 48 (wherein it is supplemented by recycle desorbate and purge medium from bed 18 during regeneration) and steam heater 50 wherein the temperature is raised to 230° F. and the pressure increased to 400 psia to maintain the fluid stream in the liquid phase, valve 52, line 54, valve 56 and line 36 downward into bed 18. In passing through bed 18, the regeneration medium heats the adsorbent and methanol is desorbed and carried out of the bed through line 30, valve 38, line 26 and line 58. The flow through line 58 is split into two streams—one stream passing through valve 60, heat exchanger 46, line 70, cooler 72, line 74 into reactor feed surge drum 76. At the end of the first 60 minutes of the overall process cycle described herein, valve 52 is closed and the flow of the regeneration medium by-passes heater 50 and instead passes through valve 78 to line 54. This is a heat conservation measure which takes advantage of the high temperature of the effluent from the bottom of bed 18 at this time. The combined streams through lines 48 and from pump 68 is about 170° F. at this point, so that the adsorbent at the top of bed 18 begins to cool down while heating the regeneration medium, thus enabling the continued stripping of methanol from the lower portion of bed 18. This "pre-cool" step is continued for five minutes, at the end of which the cooling step in bed 18 begins at sixty five minutes into the overall cycle. For this purpose the flow of regeneration medium through line 40 is diverted through line 80, valve 82, line 84 and thence through cooler 72. A portion of the stream emerging from cooler 72 is passed to reactor surge drum 76, and the remainder is passed through valve 86, line 88, line 66, pump 68, valve 78, line 90, valve 92 and line 30 into the bottom of bed 18. As this stream passes through the adsorbent it becomes heated and the adsorbent cooled. The heated bed effluent passes through line 36, valve 94, line 24, line 58, valve 60 and is partially cooled in heat exchanger 46. During passage from heat exchanger 46 through line 70, the cool down medium is supplemented by flow of regeneration medium through line 84, and the combined stream further cooled by passage through cooler 72. This operation is continued until th eightieth minute of the overall cycle. The next thirty minute period is the displacement step in bed 18. For this purpose feedstock flow through line 10 is directed through valve 96, line 30 into bed 18. Regeneration cool down medium is displaced from bed 18 through line 36, valve 94, line 24, line 26, valve 98 and line 14 into the bottom of bed 16 wherein it displaces feedstock contained in the bed void space upward over the unspent adsorbent at the top of bed 16. The effluent from bed 16 is product $C_4$ hydrocarbons which are removed from the system through line 20, valve 32 and line 34. Thereafter, a fifty minute adsorption step is carried out in bed 18 in the manner as described above for bed 16, and a fifty minute regeneration (including cool down) is carried out in bed 16 in the manner as described above for bed 18. As will be immediately apparent to those skilled in the art from the foregoing description, that the time required in the prior known processes for a discrete step in which void space feedstock is drained from the bed prior to commencing the regeneration step is saved by the present process wherein the draining of feedstock becomes, in effect, the terminal part of the adsorption step. Similarly, the conventional bed filling step in which the regeneration medium is removed from the bed and replaced with liquid phase feedstock is, in the present process the terminal part of the regeneration procedure. Thus the cycle times are significantly shortened.

Figure 2:
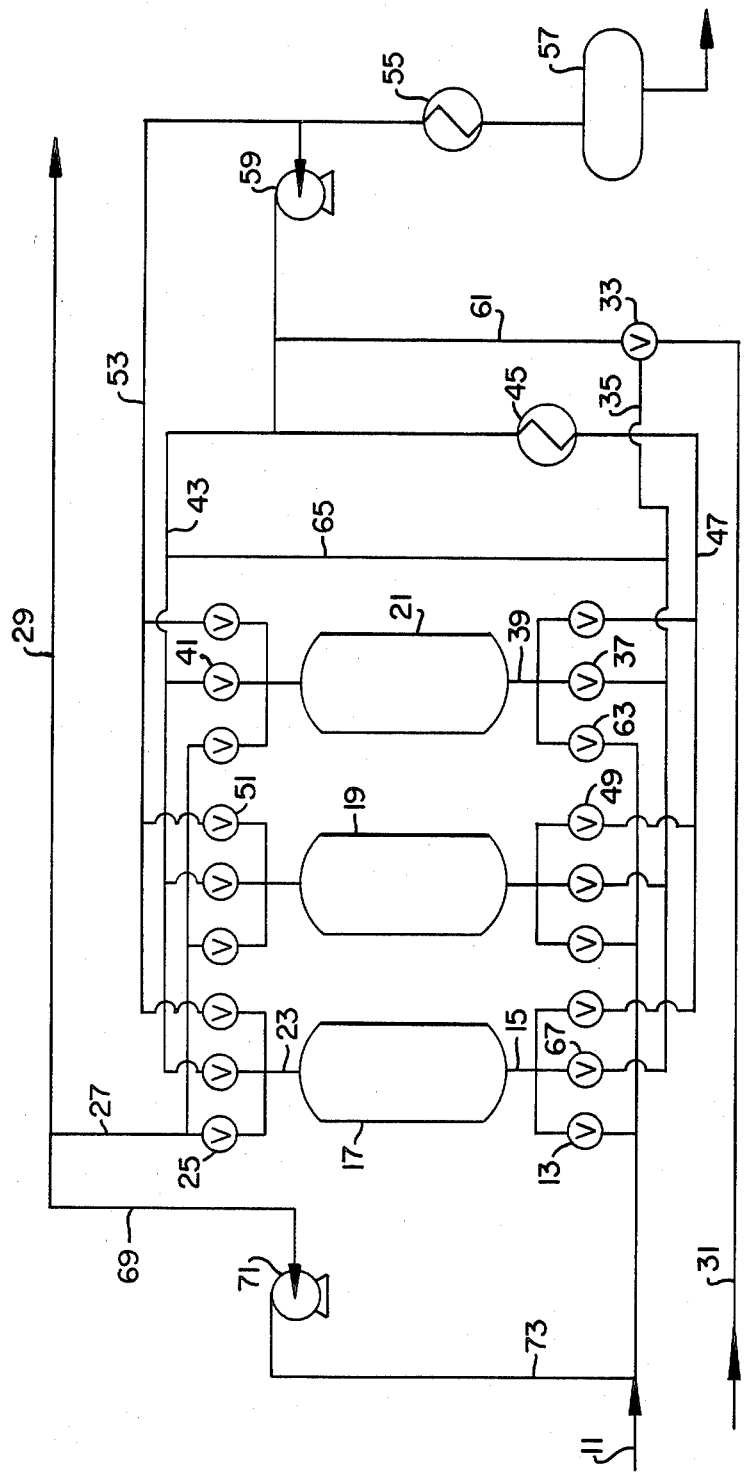
FIG. 2 is a similar schematic flow diagram for an adsorption system comprising three adsorption beds.

It is preferred in the practice of the present process to employ an adsorption system containing three adsorbent beds. A process embodiment of this kind is illustrated below with reference to FIG. 2 of the drawings. Using the same feedstock as described above in conjunction with the operation of the two bed system, the methanol-containing $C_4$ and $C_5$ raffinate is passed into the system through line 11, valve 13 and line 15 into bed 17 which is engaged in an adsorption-purification step. At the same time bed 19 is undergoing the heating phase of the regeneration step and bed 21 is undergoing bed cool down in preparation for the beginning of another adsorption regeneration cycle. During passage through bed 17, the methanol of the feedstock is adsorbed and the product hydrocarbon stream passes from bed 17 through line 23, valve 25, line 27 and leaves the system via line 29. Simultaneously, bed 21 which is initially at a temperature of about 250° F. is being cooled by the passage therethrough of hydrocarbon MTBE reactor feed, such feed entering the system through line 31, and passing through valve 33, line 35, valve 37 and line 39 into the bottom of bed 21. In addition to cooling the adsorbent of bed 21, the cold hydrocarbon reactor feed entering at the bottom displaces the hot hydrocarbon reactor feed remaining at the end of the previous heating phase therein. The hydrocarbon effluent from bed 21 passes through valve 41 and line 43 and is initially at a temperature of about 220°-245° F. The flow of this effluent continues to heater 45 wherein the temperature is again raised to 250° F. and thence through line 47 and valve 49 into the bottom of bed 19. Bed 19 has just previously undergone an adsorption displacement step and is filled with cold reactor feed at the time introduction of the effluent from bed 21 begins. The passage of the 250° F. stream into bed 19 simultaneously begins to heat the adsorbent in bed 19 and displaces the cold hydrocarbon reactor feed leaves bed 19 through valve 51 and passes through line 53 and is subsequently divided into two portions, one of which is cooled in cooler 55 and is collected in surge drum 57 for subsequent passage to the MTBE reactor. The other portion passes through pump 59 and line 61 to valve 33 wherein it is combined with hydrocarbon reactor feed from line 31 and fed to the bottom of bed 21. The foregoing procedure continues until an increase in the methanol content of the reactor feed effluent from the top of bed 19 begins to increase. Thereafter flow of the entire effluent from bed 19 is passed to surge drum and none is recycled to bed 21 via pump 59, line 61, valve 33, line 35, valve 37 and line 39. Operation in this manner continues until the outlet temperature of bed 21 begins to decrease, i.e., the cooling front just starts to leave the bed. Thereafter the cycle is completed as follows:

With respect to bed 19, the heating step is completed by the flow of hydrocarbon reactor feed through line 31, valve 33, line 61, heater 45, line 47 and valve 49 into the bottom of bed 19, this feed stream being supplemented by any recycle feed from the top of bed 19 passing through line 53 and pump 59. Whether any effluent from bed 19 is thusly recycled to the bottom of bed 19 is dependent on other process variables.

With respect to beds 17 and 21, the raffinate feedstock entering the system through line 11 is passed to bed 21 through valve 63 and line 39. As the feedstock moves through bed 21, the methanol contained therein is removed by adsorption. The methanol-free hydrocarbon product thus produced displaces the hydrocarbon reactor feed present in the bed void space as a consequence of the immediately preceding bed cool down step (although the bed may still be quite warm), and this displaced reactor feed leaves the top of bed 21 through valve 41 and is fed to the bottom of bed 17 through line 43, line 65, line 35, valve 67 and line 15. Entering the bottom of bed 17 the reactor feed displaces the raffinate remaining in bed 17 at the end of the immediately prior adsorption step therein. The quantity of adsorbent in bed 17 is such that the capacity remains to remove any methanol remaining in the raffinate as it is displaced from the bed. The methanol free hydrocarbon product leaves bed 17 through line 23, valve 25 and line 27. The bulk of the product is removed from the system through line 29, and a proportion thereof is recycled to the raffinate feed through line 69, pump 71 and line 73. By means of pump 71 the displacement step can be carried out in a time interval that is significantly less than would be required to carry out the displacement step in the absence of recycling the adsorption product. Also, since the amount of raffinate (from the MTBE distillation unit) can constitute a relatively small part of the combined raffinate/product recycle stream, the time required for the displacement step can be fixed even though some fluctutations occur in the flow rate of the raffinate feedstock entering the system through line 11 during the displacement step in each of the three adsorption beds.

As will be apparent from the foregoing, a significant attribute of the present process operation is the ease with which the product flow rates can be maintained constant. This is due to the fact that even using a two bed adsorption system one of the beds is always producing product, whether by virtue of being engaged in the adsorption separation step per se or as a result of the displacement step. In conventional processes involving the usual drain and fill operations this is usually not the case.

Other advantages will be obvious to those skilled in the art, particularly when the peculiarities of specific feedstocks and regeneration media are taken into account.

What is claimed is:

1. An adsorption process comprising the steps of:
   (a) providing an adsorption system comprising at least a first and second fixed adsorbent bed containing adsorbent particles and having void space not occupied by the adsorbent particles:
   (b) passing as a feedstock into the first of said adsorbent beds a mixture of at least two molecular species in the liquid phase of which at least one is selectively absorbed by the absorbent particles, and recovering from the bed a product having a lower concentration of the adsorbed species than the feedstock:
   (c) terminating the passage of feedstock into said first adsorbent bed at a time when the adsorbent therein retains sufficient capacity to adsorb the desired amount of the molecular species from the feedstock contained within the first said adsorbent bed, and directing the flow of the said feedstock in the liquid phase into the second of said fixed adsorbent beds, said second bed at the beginning of passage of feedstock thereinto containing in the void space a liquid purge medium different from the feedstock in step (b);
   (d) recovering said liquid purge medium from the void space of said second bed by displacement as a result of the passage of feedstock thereinto and passing said displaced liquid purge medium directly to the said first bed after the passage of feedstock into said first bed has been terminated in accordance with the process step (c) above, whereby the feedstock in the void space of said first bed is purged therefrom and
   (e) continuing the flow of feedstock into said second bed in the same manner as into said first bed in (b) and recovering a product of essentially the same composition as is recovered in step (b).

2. Process according to claim 1 wherein the adsorbent in the first and second fixed adsorbent beds is a zeolitic molecular sieve.

3. Process according to claim 1 wherein the adsorbent in the first and second fixed adsorbent beds is a silica gel.

4. Process according to claim 1 wherein in the displacement of liquid purge medium of step (d) is accomplished using a portion of the liquid product of step (b) in combination with the feedstock.

5. Process according to claim 1 wherein in step (a) the adsorption system comprises three adsorption beds.

6. Process according to claim 1 wherein in step (d) wherein the flow of displaced liquid purge medium from the void space of said second bed to said first bed is in the same direction as the flow in step (b).

7. Process according to claim 1 wherein the feedstock comprises a mixture of at least one normal hydrocarbon having four carbon atoms with an alkanol having from one to five carbon atoms, and the pure medium is a mixture of hydrocarbons.

8. Process according to claim 4 wherein the alkanol is methanol.

* * * * *